US006463320B1

United States Patent
Xue et al.

(10) Patent No.: US 6,463,320 B1
(45) Date of Patent: Oct. 8, 2002

(54) CLINICAL RESEARCH WORKSTATION

(75) Inventors: Qiuzhen Xue, Germantown, WI (US); Shankara B. Reddy, Cedarburg, WI (US)

(73) Assignee: GE Medical Systems Information Technologies, Inc., Waukesha, WI (US)

( * ) Notice: Subject to any disclaimer, the term of this patent is extended or adjusted under 35 U.S.C. 154(b) by 0 days.

(21) Appl. No.: 09/469,824

(22) Filed: Dec. 22, 1999

(51) Int. Cl.[7] .................................................. A61B 5/04
(52) U.S. Cl. ...................................................... 600/523
(58) Field of Search ......................... 128/922; 600/523, 600/300, 301, 509, 525; 702/71, 72, 73, 74, 79; 607/27, 30

(56) References Cited

U.S. PATENT DOCUMENTS

| | | | | | |
|---|---|---|---|---|---|
| 5,560,368 | A | * | 10/1996 | Berger | 128/703 |
| 5,724,985 | A | * | 3/1998 | Snell et al. | 128/697 |
| 6,224,549 | B1 | * | 5/2001 | Drongelen | 600/300 |
| 6,321,113 | B1 | * | 11/2001 | Parker et al. | 607/5 |
| 6,322,502 | B1 | * | 11/2001 | Schoenberg et al. | 600/300 |

* cited by examiner

Primary Examiner—Jeffrey R. Jastrzab
Assistant Examiner—Frances P. Oropeza
(74) Attorney, Agent, or Firm—Ostrager Chong & Flaherty LLP

(57) ABSTRACT

An apparatus and a method for taking multiple physiological signals (e.g., ECG waveforms) from different sources as input, applying multiple algorithms in its core and generating results which are exported for use in clinical studies and research. The apparatus has a built-in database and a built-in spreadsheet to provide a unified platform for all clinical research in the medical field, including, but not limited to, clinical core laboratory work and high-end clinical research.

40 Claims, 9 Drawing Sheets

FIG. 4

| A1 | | 23 | | | | | | | |
|---|---|---|---|---|---|---|---|---|---|
| | A | B | C | D | E | F | G | H | I |
| 1 | 23 | | | | | | | | |
| 2 | 101 | Sinus tachycardia | | | | | | | |
| 3 | 1680 | with 1st degree AV block | | | | | | | |
| 4 | 780 | Possible | | | | | | | |
| 5 | 830 | Interior infarct | | | | | | | |
| 6 | 1081 | possibly acute | | | | | | | |
| 7 | | Marked ST abnormality, possible anterolateral subendocardial injury | | | | | | | |

18

12SL Statement / 1012SL / Selection paras / Sheet1

46    48    50

| | A | B | C | D | E | F | G | H | I | J | K |
|---|---|---|---|---|---|---|---|---|---|---|---|
| 1 | | | | | | | | | | | |
| 2 | | Age | Weight | vrate | arate | pr | qrsd | qt | | | |
| 3 | | | | | | | | | | | |
| 4 | | pax | qrsax | tax | | | | | | | |
| 5 | | | | | pdur | qtc | | | | | |
| 6 | | scode | qrstime | qrstype | | | | | | | |
| 7 | | | | | | | | | | | |
| 8 | | | | | | | | | | | |
| 9 | | Arrays of individual lead amplitudes & durations | | | | | | | | | |
| 10 | maxra | I | II | III | aVR | aVL | aVF | V1 | V2 | V3 | V4 |
| 11 | pona | I | II | III | aVR | aVL | aVF | V1 | V2 | V3 | V4 |
| 12 | pa | I | II | III | aVR | aVL | aVF | V1 | V2 | V3 | V4 |
| 13 | pd | I | II | III | aVR | aVL | aVF | V1 | V2 | V3 | V4 |
| 14 | ppa | I | II | III | aVR | aVL | aVF | V1 | V2 | V3 | V4 |
| 15 | ppd | I | II | III | aVR | aVL | aVF | V1 | V2 | V3 | V4 |
| 16 | qa | I | II | III | aVR | aVL | aVF | V1 | V2 | V3 | V4 |
| 17 | ra | I | II | III | aVR | aVL | aVF | V1 | V2 | V3 | V4 |
| 18 | rd | I | II | III | aVR | aVL | aVF | V1 | V2 | V3 | V4 |
| 19 | sa | I | II | III | aVR | aVL | aVF | V1 | V2 | V3 | V4 |
| 20 | sd | I | II | III | aVR | aVL | aVF | V1 | V2 | V3 | V4 |
| 21 | rpa | I | II | III | aVR | aVL | aVF | V1 | V2 | V3 | V4 |
| 22 | rpd | I | II | III | aVR | aVL | aVF | V1 | V2 | V3 | V4 |
| 23 | spa | I | II | III | aVR | aVL | aVF | V1 | V2 | V3 | V4 |

12SL Statement / I012SL / Selection paras / Sheet

Rest ECG Database Select

DB Class [AMI ▼]

Filters

| | Fields | Conditions |
|---|---|---|
| 1 | NONE ▼ | |
| 2 | vrate ▼ | <100 |
| 3 | Qrsd ▼ | <120 |
| 4 | NONE ▼ | |
| 5 | NONE ▼ | |

Date. Time (Example: 1/30/96 9:35:20 AM)
From: [ ]  To: [ ]

Sorting
[Patient_ID ▼]

[ OK ]   [ Cancel ]

FIG.8

CLINICAL RESEARCH WORKSTATION

FIELD OF THE INVENTION

This invention relates to analysis of electrocardiograms and other physiological data.

BACKGROUND OF THE INVENTION

Currently there is a lack of tools for physicians and biomedical scientists to do research work with a large amount of physiological data acquired by medical devices. For example, tools do not exist for exporting measurements and waveform data from the original files and evaluating the value of new clinical parameters and algorithms such as QT dispersion, T wave alternans, signal averaging, and heart-rate variability. The currently employed manual methods of extracting measurements and data are laborious and time-consuming and they suffer from high intra- and inter-observer variability and poor reproducibility. A semi-automatic system with options for physician's review and editing would greatly facilitate clinical research work in cardiology and other branches of medicine.

SUMMARY OF THE INVENTION

The present invention is directed to an apparatus and a method for taking multiple physiological signals from different sources as input, applying multiple algorithms in its core and generating results which are exported for use in clinical studies and research. The apparatus has a built-in database and a built-in spreadsheet to provide a unified platform for all clinical research in the medical field, including, but not limited to, clinical core laboratory work and high-end clinical research.

The preferred embodiment of the invention is a clinical research workstation capable of handling a wide range of physiological signals including, but not limited to, resting electrocardiogram (ECG), ambulatory ECG, stress ECG, signal-averaged ECG, intra-cardiac electrical and hemodynamic signals, pulse oximetry signals, blood pressure signals, cardiac output signals, electroencephalogram, electro-oculogram, etc. Analysis of each of these physiological signals is supported in one or more separate modules. The research workstation in accordance with the preferred embodiment is also capable of accepting physiological data from a variety of data sources, such as medical devices and systems, including, but not limited to, electrocardiographs, continuous 12-lead ST segment monitors, Holter recorders, stress ECG systems, defibrillators, patient monitors, home health-care devices, medical data storage/management systems, etc.

In accordance with the preferred embodiment, the research workstation has the capability to export any user-selected data in many output formats and different configurations. Output data will include, but is not limited to, patient demographic information, measurements and waveform signals of both processed and raw data stored in the data file. In addition to the data stored in the file, many measurements and waveforms will also be generated by processing the stored data in the research workstation. Users can select any combination of measurements from a built-in spreadsheet by highlighting the ones they need. A batch processing can be used to export the patient demographics, measurements and/or waveform data from the whole directory or a selected database from a built-in Open Database Connectivity (ODBC) database.

With various physiological data as input from multiple data sources, the system will be able to evaluate new parameters using different algorithms. For example, some high-risk cardiac disease indicators such as signal-averaged ECG parameters, QT dispersion, T wave alternans, and heart rate variability, all from the same patient, can be evaluated at the same time. Algorithms which can be optionally built into the research workstation include, but are not limited to, the following: (1) new measurements with and without user-defined re-analysis from physiological data including, but not limited to, resting ECG, ambulatory ECG, stress ECG, intra-cardiac electrical and hemodynamic signals, and ECG, pulse oximetry and blood pressure signals from neonatal, pediatric and adult patient monitors and defibrillators; (2) interpretation and re-analysis of resting ECG; (3) QT dispersion and T wave alternans; (4) multi-lead vector ECG analysis; (5) signal-averaged ECG processing; (6) ECG mapping and modeling; (7) signal filtering and spectral analysis; and (8) heart-rate variability.

In accordance with a further aspect of the preferred embodiment, the research workstation has a built-in ODBC database (Microsoft Access database). The key parameters are stored automatically into the database, and they can be retrieved, sorted and filtered within the system. With this database, reviewing and editing the measurements and interpretation are very convenient. For example, a few simple operations such as, clicking "go forward" and "go backward" buttons will lead the researcher through physiological data files one by one.

In addition, the system has a built-in spreadsheet for selecting for export, reviewing and plotting any of the measurements. The spreadsheet is compatible with standard data analysis software, including, but not limited to, Microsoft Excel and SAS (statistical analysis software) packages, and can be directly saved as a file compatible with standard data analysis software. Researchers can perform most analysis and plotting inside the system, and the spreadsheet interacts with the builtin database seamlessly. A trend of a selected group of physiological parameters/measurements can also be plotted.

The clinical research workstation provides standardized coding/scoring of physiological data, including, but not limited to, Minnesota code, and NOVACODE for resting ECG. The research workstation also provides essential functions needed in core laboratories for clinical studies, including, but not limited to, measuring, reviewing and editing of modifiable time markers in physiological waveforms such as waveform onsets, peaks and offsets, re-analysis based on user-modified markers and serial comparison.

The research workstation software disclosed herein can help physicians advance studies in areas such as disease epidemiology, pharmaceutical research and out-come-based analysis. Using this software, physicians can transform a standard computer with a database program such as Microsoft Access and a speadsheet program such as Microsoft Excel into an ECG research workstation that allows them to quickly and easily study large volumes of ECG data. The research workstation software enables physicians to store, access, review and plot ECG data with point-and-click efficiency.

BRIEF DESCRIPTION OF THE DRAWINGS

FIGS. 4 and 5 are schematics depicting a 12SL Statement and an array of selectable parameters for export respectively displayed in spreadsheet format in the Results window in accordance with the preferred embodiment of the invention.

FIG. 7 is a schematic depicting a Database window in accordance with the preferred embodiment of the invention.

FIG. 8 is a schematic depicting a "Rest ECG Database Select" window in accordance with the preferred embodiment of the invention.

DETAILED DESCRIPTION OF THE PREFERRED EMBODIMENTS

Figure 1:
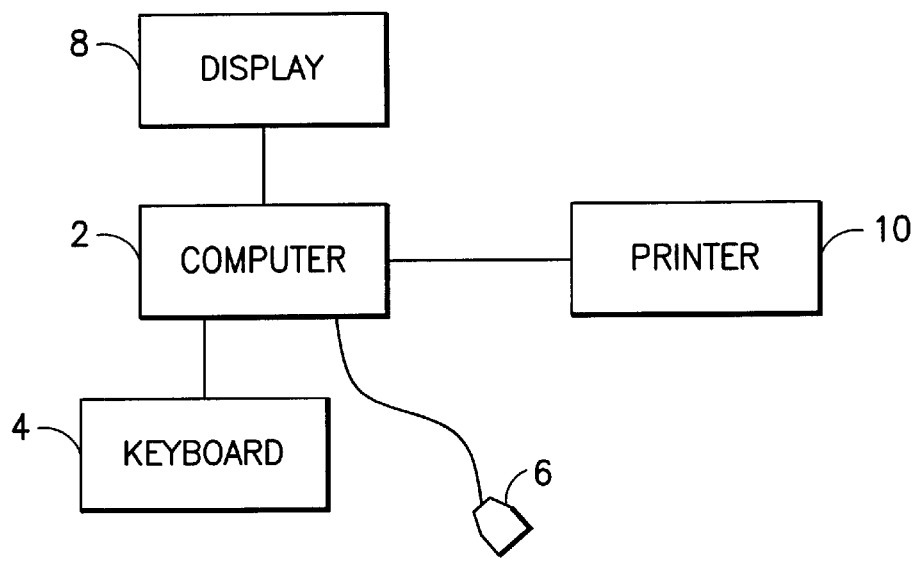
FIG. 1 is a block diagram showing a conventional personal computer system which can be programmed with research workstation software.

The preferred embodiment of the invention comprises research workstation software installed on a computer system. A typical computer system is generally depicted in FIG. 1 and comprises a computer 2, a keyboard 4, a mouse 6, a display monitor 8 and a printer 10. The software of the preferred embodiment requires the following software: an operating system such as Microsoft Windows 95 or 98, or Windows NT 3.51 or 4.0; a database program such as Microsoft Access for Windows; and a spreadsheet program such as Microsoft Excel for Windows. Although the workstation of the invention can be used to perform clinical research on physiological data including, but not limited to, resting ECG, ambulatory ECG, stress ECG, intracardiac electrical and hemodynamic signals, and ECG, pulse oximetry and blood pressure signals, the preferred embodiment will be disclosed in the context of ECG signals for the sake of simplicity, with the understanding that other types of physiological data can be processed in a similar manner. The ECG research workstation incorporates ECG analysis programs such as 12SL from GE Marquette Medical Systems, Inc., which is a computer program for analyzing simultaneously acquired 12-lead ECGs. It makes precise measurements of recorded cardiac signals, then provides an interpretation of the ECG waveforms using ECG interpretation criteria for both rhythm and morphology.

The clinical research workstation software in accordance with the preferred embodiment is used to review and export ECG waveforms, interpretations and measurements for research purposes. The main functions of the research workstation software include: (1) acquiring ECG files from devices and systems; (2) reviewing the ECG waveforms, interpretation and measurements; (3) selecting the ECGs based on user-defined criteria (e.g., age, gender, measurements, interpretation); (4) re-measuring and re-analyzing stored. ECGs; and (5) exporting the analysis, measurements and waveform data from the stored ECG files or re-measured/re-analyzed results in a user-selected format. As used herein, the term "database" includes patient information, parameter data and path names for locating raw ECG (actual waveform) files stored in memory. In addition, the terms "record" and "file" will be used interchangeably. The terms "class" and "group" will be used interchangeably to refer to groups of records/files in the database.

Figure 2A:
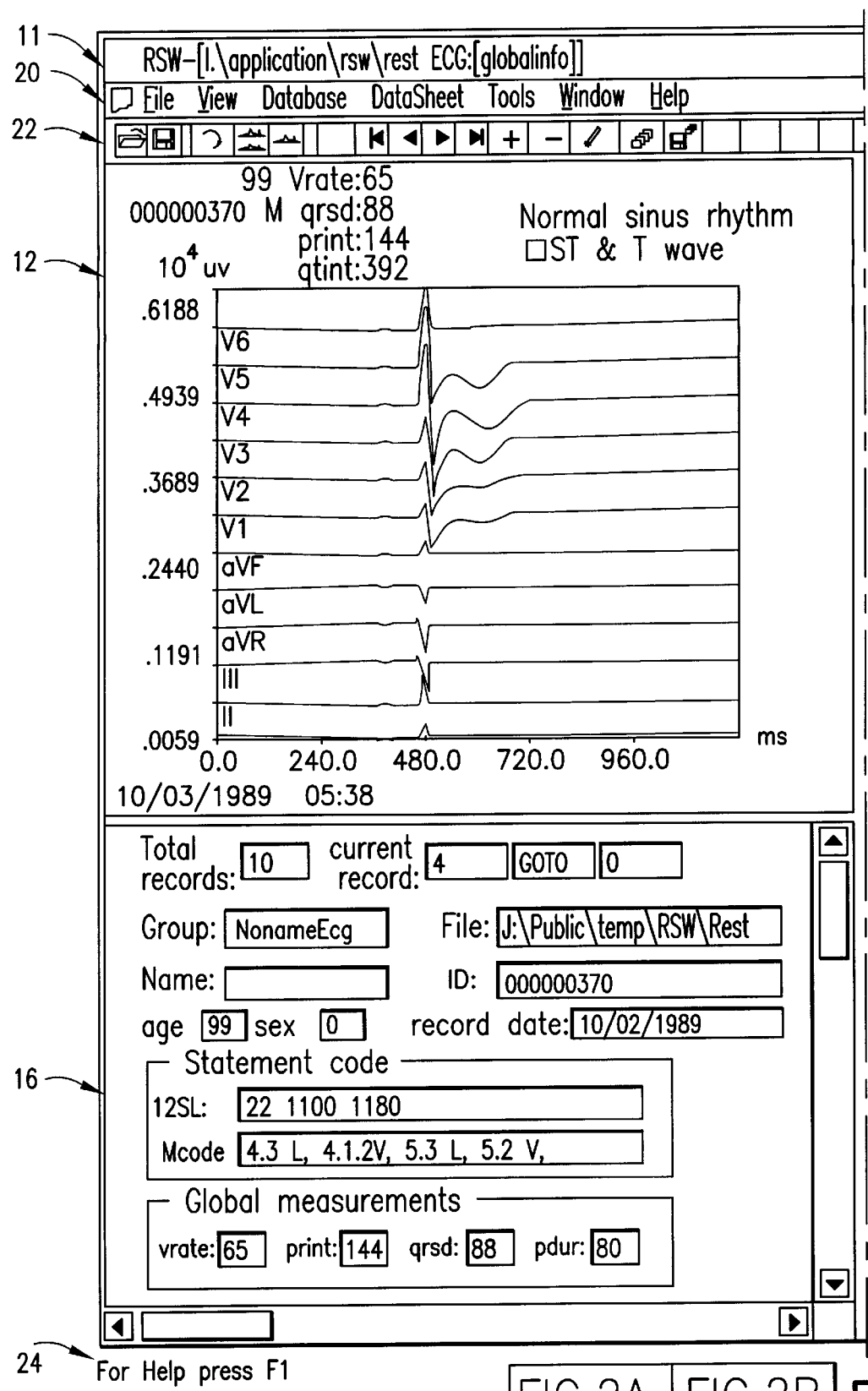
FIG. 2 is a schematic depicting an ECG research workstation window in accordance with the preferred embodiment of the invention.
Figure 2B:
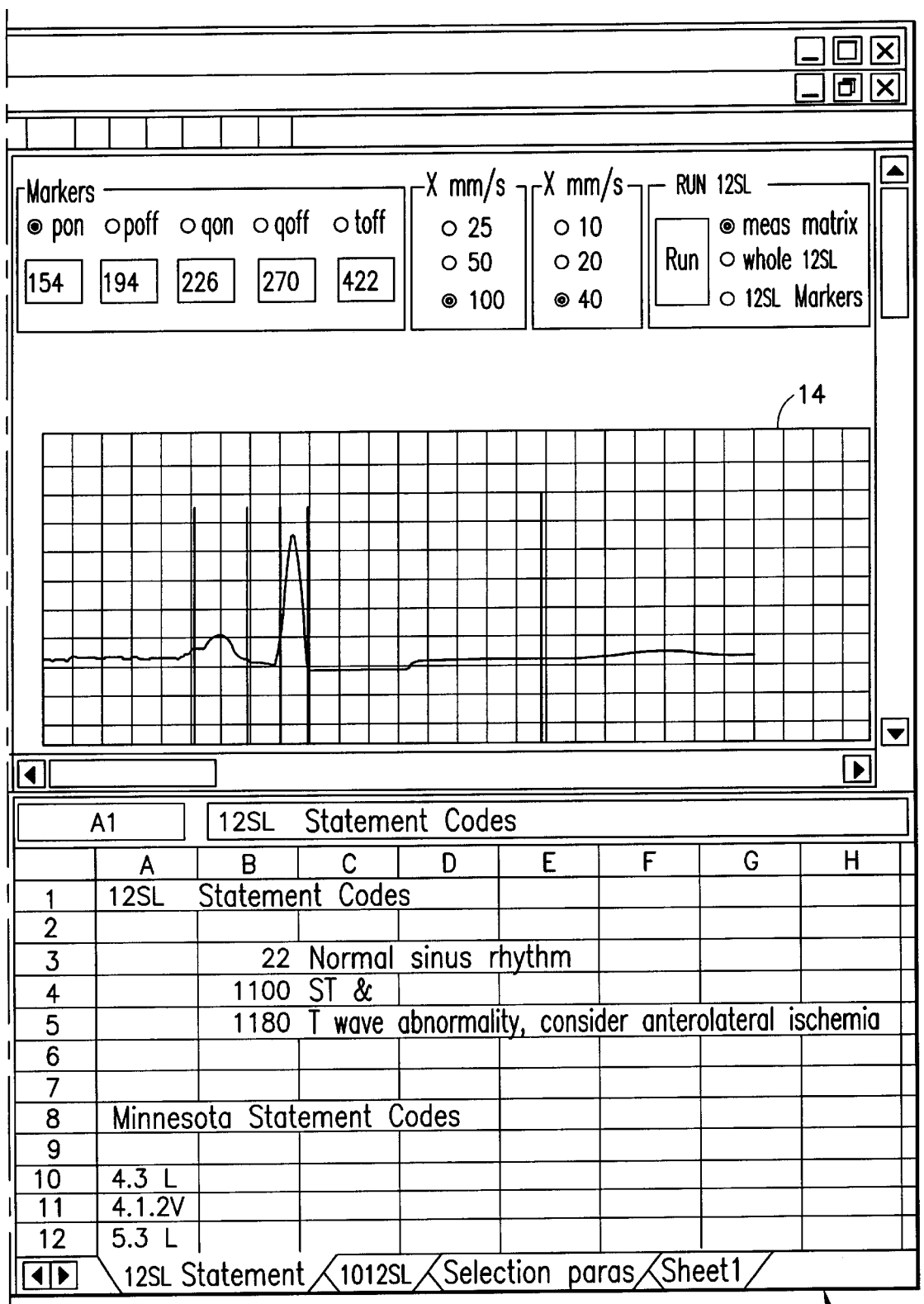

An ECG research workstation window is presented in FIG. 2, showing the window as it appears on the computer display screen when the computer is running the research workstation software of the preferred embodiment. The title bar 11 contains the title name for the ECG research workstation work area, and the close, maximize and minimize buttons for the ECG research workstation window. As seen in FIG. 2, the window is divided into four quadrants: the upper left-hand quadrant is the Signal window 12, the upper right-hand quadrant is the Modify window 14, the lower left-hand quadrant is the Database window 16, and the lower right-hand quadrant is the Results window 18. The windows can be resized by placing the cursor over-the intersection of the window borders or over a horizontal or vertical window border and then dragging the cursor using the mouse 6. The Signal window 12 displays 12-lead ECG data as a standard, median or rhythm strip. The Modify window 14 displays and modifies the appearance of a selected signal from the Signal window 12. The Database window 16 displays the records of the Microsoft Access database. With the Database window active, the user can: (1) perform 12SL re-analysis on a group of ECGs automatically; (2) save the results to the database; and (3) review the data. The Results window 18 displays 12SL results and parameters. The menu bar 20 displays pulldown menu options. The available pulldown menus include File, View, Database, DataSheet, Windows and Help menus. The tool bar 22 provides quick access to commonly used features. The buttons (i.e., tool icons) on the tool bar are available depending upon the function being performed and which window is active. Most of these functions are also available from the pulldown menus. The status bar 24 displays research workstation status information.

The tool bar 22 preferably includes an Open button which opens an ECG file and a Save button which saves the current ECG file. ECG files can also be opened and saved by clicking on Open and Save selections in the File menu. When an ECG file is opened, the ECG waveforms appear in the signal window 12, a selected one of those displayed wave-forms appears in the Modify window 14, the raw waveform data is processed using the ECG analysis program in accordance with the option selected in the Modify window, and the analysis results are displayed in spreadsheet format in the Results window 18. Major parameters such as patient name, ID, and age appear in the Database window 16 when an ECG file is opened.

As seen in FIG. 2, the Signal window 12 appears in the upper left-hand corner of the ECG research workstation window. It displays the raw, unprocessed waveforms. When the Signal window 12 is active, the ECG signals from an opened ECG file can be displayed in one of three formats, the format being selectable by clicking on a corresponding button on the tool bar menu 22, i.e., the Standard ECG Plot, Median ECGs and Rhythm ECGs buttons. The Standard ECG Plot button displays a standard ECG in the Signal window, which is in the format of 2.5 sec by 4, plus 10 sec of lead II and v.1. The Median ECGs button displays the median beats formed by the ECG analysis program. The Rhythm ECGs button displays the 10-sec 12-lead rhythm ECG in the Signal window.

An individual waveform displayed in the Signal window 12 can be selected for display in the Modify window 14. An individual waveform is selected by clicking on it, or by using the up and down keys on the keyboard 4. Pressing the PgUp key selects the first waveform; pressing the PgDn key selects the last waveform. A selection bar (not shown), appearing in the form of a vertical line, is used to select a specific point in time on the ECG waveform displayed in the Signal window 12. The selection bar can also be used to take measurements. Whenever the selection bar in the Signal window 12 is moved, data changes in the status bar 24 to reflect the new position. The computerized analysis, measurement and interpretation information is provided by the ECG analysis program.

Figure 3:
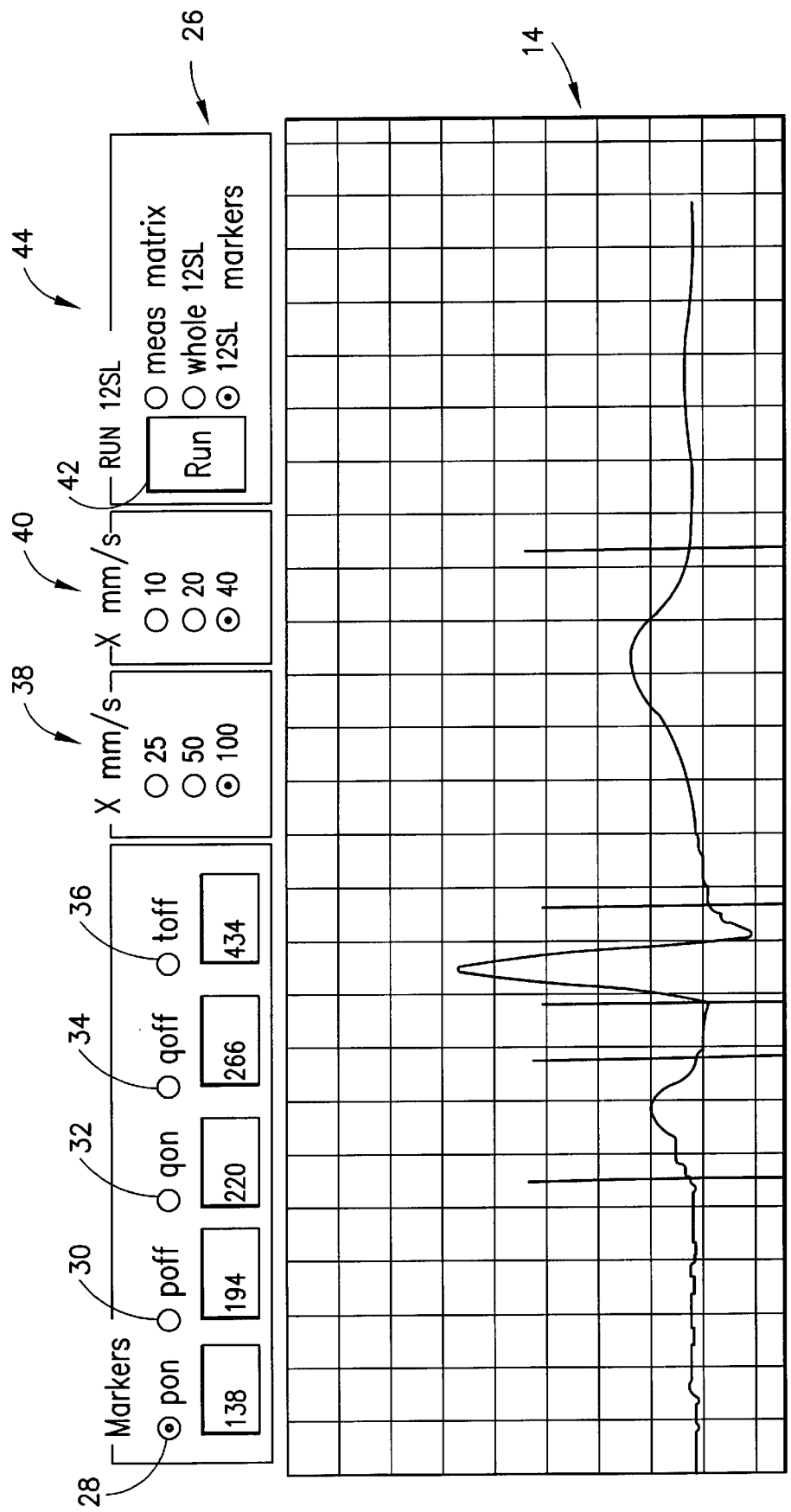
FIG. 3 is a schematic depicting a Modify window in accordance with the preferred embodiment of the invention.

The Modify window 14 provides individual lead waveform demarcation information and variable display gains, and allows for manual manipulation of automatic demarcation points and complete or partial reanalysis of the ECG data by the ECG analysis program. The specific lead displayed in this window is selected from the Signal window, as previously described. A Modify window tool bar 26 is displayed directly above the displayed signal, as seen in FIG. 3. The Modify window includes a multiplicity of virtual radio buttons. The radio button 28 (labeled "pon") is used to modify the P onset markers; the radio button 30 (labeled "poff") is used to modify the P offset markers; the radio button 32 (labeled "qon") is used to modify the Q onset markers; the radio button 34 (labeled "qoff") is used to modify the Q offset markers; and the radio button 36 (labeled "toff") is used to modify the T offset marker. These markers appear as green lines on the ECG signal in the Modify window. The procedure for modifying these markers is as follows: (1) in the Modify window tool bar, click on the virtual radio button corresponding to the marker to be modified; and (2) drag the corresponding green line to the desired location.

In addition, the Modify window tool bar can be used to modify the time and/or amplitude resolution for the signal being displayed in the Modify window. One set 38 of virtual radio buttons is provided for changing the time resolution along the X axis; another set 40 of virtual radio buttons is provided for changing the amplitude resolution along the Y axis. The three radio buttons in set 38 correspond respectively to time resolutions of 25, 50 and 100 mm/sec. The three radio buttons in set 40 correspond respectively to amplitude resolutions of 10, 20 and 40 mm/mV. The resolution can be changed by clicking the desired resolution for either the X or Y axis or for both. In response, the signal changes to conform to the new resolutions. The grids in the Modify window do not change size.

Clicking on the Run button 42 runs the ECG analysis program in accordance with a selected one of three options: (1) for the option labeled "meas matrix", only part of the ECG analysis program is performed; (2) for the option labeled "whole 12SL", the whole ECG analysis is performed, generating more than 700 different ECG measurements; and (3) for the option labeled "12SL markers", the ECG analysis program reanalyzes using the modified markers. When an ECG file is opened, the raw ECG data will be automatically processed in accordance with the option previously selected in the Modify window, i.e., without the need to click on the Run button 42. The results of the analysis are automatically displayed as a spreadsheet in the Results window 18. The desired option is selected by clicking on the corresponding virtual radio button in the set 44 in the Modify window tool bar. For example, to run the ECG analysis program with modified markers, the following steps are performed: (1) click in the Modify window to activate it; (2) for each marker to be modified, click on the corresponding radio button in the Modify window tool bar and then drag the corresponding green line to the desired location; (3) select the "12SL Markers" radio button in set 44 in the Modify window tool bar; and (4) click the Run button 42. The results are displayed in the Results window 18, where they can be reviewed by the researcher.

The Results window 18 appears in the lower right-hand corner of the ECG research workstation window. To view the ECG interpretation statement(s) for the selected patient, the researcher clicks-the "12SL Statement" tab 46 in the Results window. The statement and its corresponding code are displayed as shown in FIG. 4. When the "IO12SL" tab 48 is activated, the Results window displays the measurements from resting ECGs and patient file parameters for exporting. The data display format can be selected either via buttons on the tool bar 22 or via items listed on a DataSheet menu (not shown in the drawings). Selection of Sheet on the DataSheet menu displays the exported parameters file as a spreadsheet in the Results window 18. Selection of Chart on the DataSheet menu displays the parameter data in the form of a chart. The Results window can also be used to select parameters for export. In the export parameters mode, the Results window 18 displays an array of selectable parameters, including an array of individual lead amplitudes and durations corresponding to the waveforms displayed in the Signal window 12. To view the window shown in FIG. 5, the user clicks on Select Parameters in the DataSheet menu or a corresponding button in the tool bar 22. This allows the user to select parameters to store in an external file by clicking on the desired parameters. The selected parameters are highlighted. In the example shown in FIG. 5, the selected parameter is indicated by the surrounding rectangular box 52. In response to clicking on Done Parameters Selection! in the DataSheet menu, a dialog box (not shown) appears on the display, asking the user whether the parameters should be exported now. The user clicks Yes to save the file. Then a Save As dialog box (not shown) appears. The user then selects the appropriate directory location and types in the file name. The user then clicks Save to save the file. A Select ECG Source box (not shown) appears having two virtual radio buttons, one labeled "From whole directory" and the other labeled "From ECG database". Selecting "From whole directory" will extract the ECG parameters from all folders in a selected directory. Selecting "From ECG database" will extract the ECG parameters from a selected database class. The ECG parameters are saved when an OK button in the Select ECG Source is clicked on. The exported parameters file can be viewed through the Selection Paras tab 50 in the Results window, e.g., in response to selection of Read Parameters in the DataSheet menu.

Figure 6:
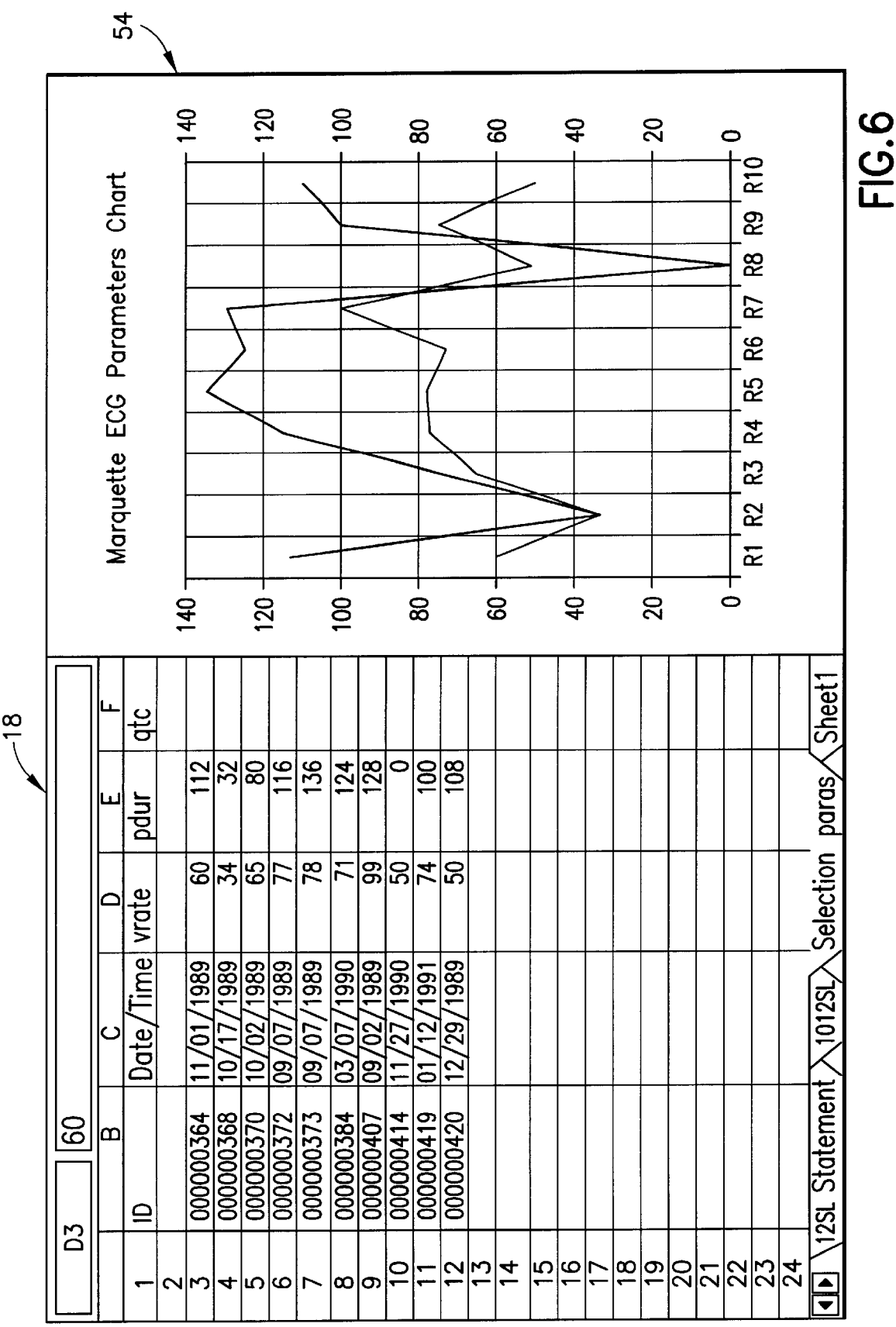
FIG. 6 is a schematic depicting a built-in spreadsheet and chart displayed in the Results window.

In addition, parameters can be viewed in chart form by linking the spreadsheet data to a chart. The procedure for viewing parameters in chart form is as follows: (1) highlight the region in the Results window which is to be linked to a chart; (2) select Link Chart to Sheet on the DataSheet menu to toggle the linkage between the chart values and the chart on; and (3) select Chart on the DataSheet menu to toggle the chart display on. The selected data appears in chart form in the Results window 18, as shown by representative chart 54 in FIG. 6.

Figure 7:
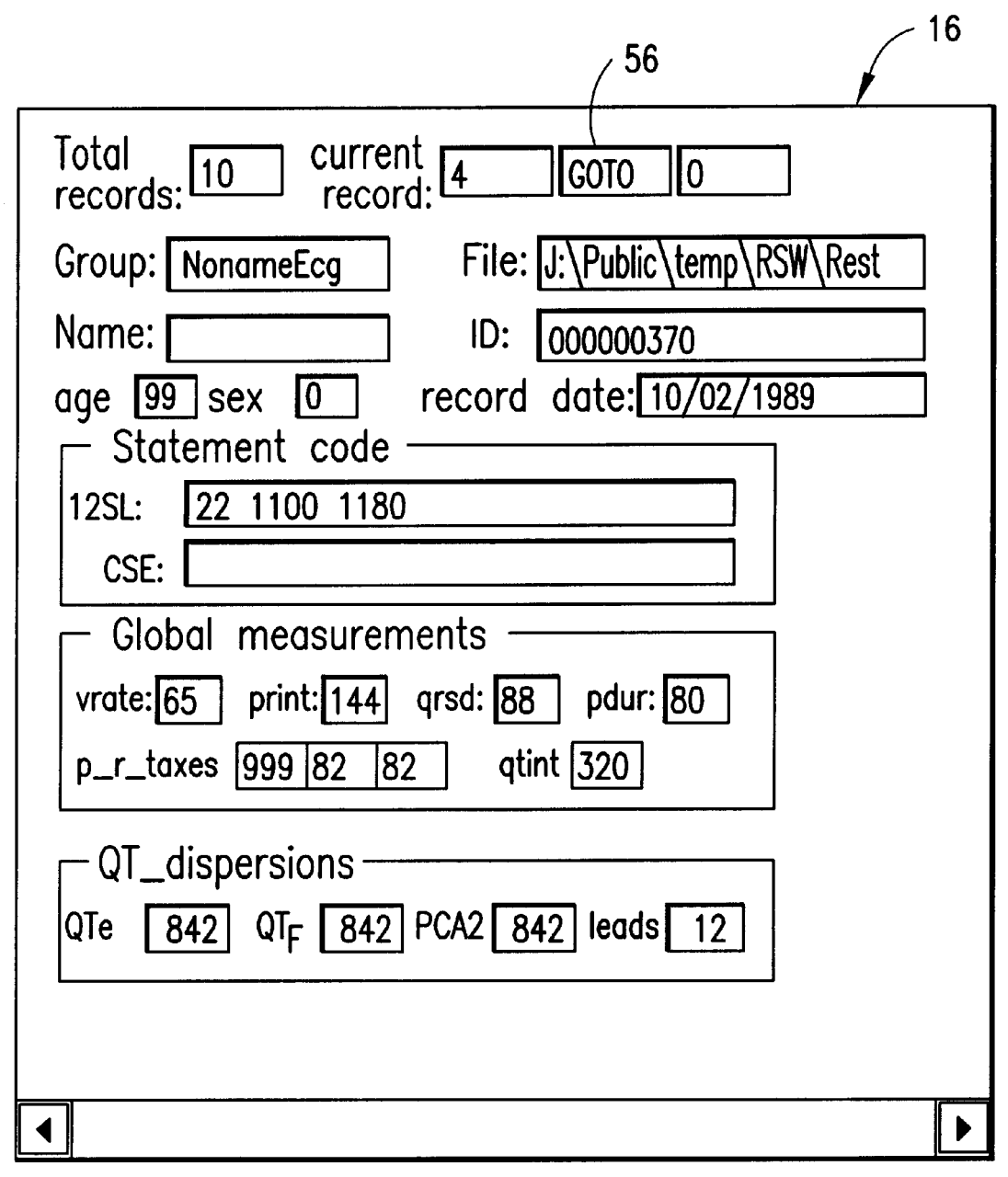

The Database window 16 appears in the lower left-hand corner of the ECG research workstation window. As shown in FIG. 7, the Database window displays information contained in the database. As previously noted, the database includes the path names to raw ECG data files, not the actual waveforms themselves. In accordance with the preferred embodiment of the invention, the Database window comprises the following fields:

Group: Used to categorize ECGs in the database.
File: Path to the directory storing the raw ECG file.
Name: Patient name.
ID: Patient identification number.
Age: Patient age.
Sex: Patient gender.
Record time: Time the ECG was taken.

Under the frame labeled "Statement code":
  12SL: ECG interpretation statement codes.
  CSE: Special coding, Minnesota coding.
Under the frame labeled "Global measurements":
  Vrate: Ventricular rate.
  PRint: PR interval.
  qrsd: QRS duration.
  Pdur: P duration.
  P-R-T axes: P, R and T axes.
  QTint: QT interval.
Under the frame labeled "QT dispersions":
  QT-end: from the beginning of the Q wave to the end of the T wave.
  QT-peak: from the beginning of the Q wave to the peak of the T wave.
  PCAS2: Use principal component analysis to describe T wave morphology.
  Leads: Number of leads
Total records: The number of records used in calculating QT dispersion.
Current record: The order number of the current record in the database.

To display a specific record in the Signal window, the user must enter the number of the record in the field next to the GOTO button 56 (see FIG. 4). Initially, the record having number 1 is displayed. Thereafter the system user can scroll through the records of the particular database group identified in the Group field by clicking on a Next Record button in the tool bar 22 (see FIG. 1). The toolbar also includes buttons for adding, deleting and modifying records in the database. During scrolling, the data in all of the windows changes to correspond to the new record, i.e., the waveforms for the next record are displayed in the Signal window, a selected one of those displayed waveforms is displayed in the Modify window, the computed parameters for those displayed waveforms are displayed in the Results window, and the patient information, Statement code, Global measurements and QT dispersions data fields in the Database window are updated. As used herein, the term "global" means that they are measured across all leads. The QT dispersion can be automatically calculated by the computer using any well-known algorithm, such as the algorithms disclosed in U.S. Pat. No. 5,792,065 and in the article by Xue et al. entitled "Algorithms for Computerized QT Analysis," J. Electrocardiology, Vol. 30 Supplement.

The database tool bar is located in the left side of the tool bar 22. The buttons of the database tool bar are available only when the Database window is active. The database tool bar includes buttons for: displaying a record of the database; adding a record to the end of the database; deleting a record from the database; replacing a current record with a modified version. In addition, the database tool bar has buttons for saving files in a whole directory to a database; performing a database search; batch exporting of patient information and/or ECG data; and batch exporting selected parameters to an external file from a selected database. When the database tool bar is active, its buttons are green. In addition, a Database menu is provided having selections corresponding to the four functions (respectively named Read Files to Database, Select Database, Export Data and Export Parameters) set forth in the next preceding sentence of this paragraph.

When the Database window is active, any group of database records can be loaded in working memory and reviewed by the user. Alternatively, the user may construct a new database group by defining a set of search parameters and then filtering out all data lying outside those parameters.

Querying the database is useful in finding ECGs that match certain criteria. A search for data satisfying these conditions can be performed as follows: (1) Click inside the Database window to activate it. (2) Click Select Database from the Database menu. The Rest ECG Database Select window (shown in FIG. 8) appears. This window is used when searching the database for records matching specified criteria. (3) If desired, select a database class from the popup menu. If this field is left blank, then all database records are available for the search. (4) Define the parameters for the ECGs that are sought. There are five filters in the Filters section of the Rest ECG Database Select window. Filter 1 is used if the searcher wants to find a record for a specific patient by name or patient identification number. The remaining filters can be used to set search parameters, e.g., the searcher can search for all ECGs in which the ventricular heart rate is less than 100 and the QRS duration is less than 120 msec. (5) Then the date and time are entered. (6) If sorting of the data is desired, a sorting methodology can be selected from the Sorting popup menu. For example, the data gathered by the search can be sorted according to Patient ID. (7) Click the OK button. The selected records from the database are loaded in working memory and appear in the Database window. The raw ECG waveforms from the first record in the group are displayed in the Signal window; a selected one of those waveforms is displayed in the Modify window; and the parameters generated by the ECG analysis program are displayed in the Results window.

Figure 9:
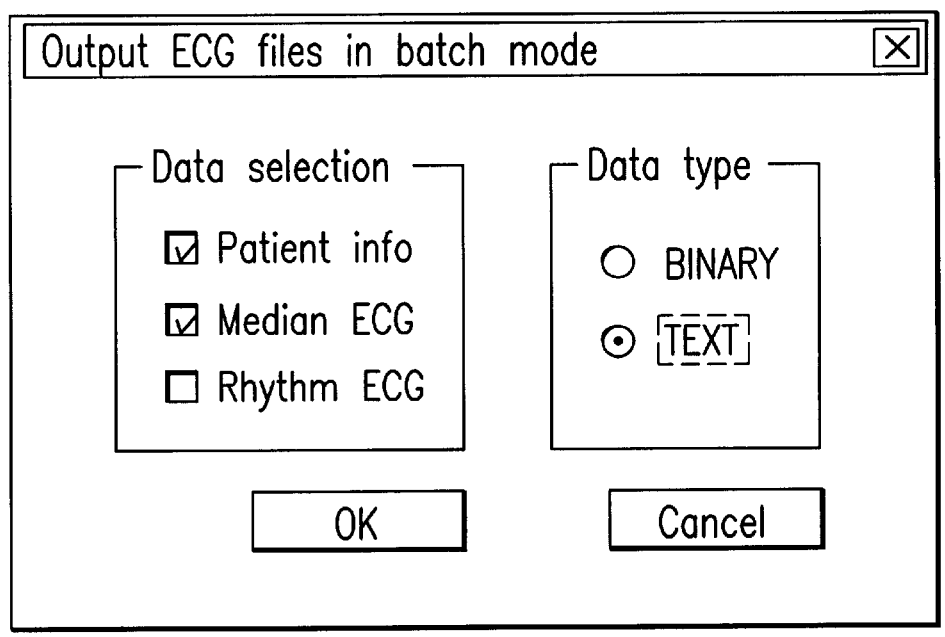
FIG. 9 is a schematic depicting an "Output ECG files in batch mode" window in accordance with the preferred embodiment of the invention.

The preferred embodiment also provides for the batch exportation of data using the following procedure: (1) Click inside the Database window to activate it. (2) Click Export Data from the Database menu. The "Output ECG files in batch mode" window (shown in FIG. 9) appears. (3) The user then selects which data he/she wants to export. The selection of "Patient info" will result in the inclusion of patient information, measurements and parameters for the 30 raw ECG files being output. The raw ECG data to be included in the batch can be either median or rhythm ECG signal, depending on which of the corresponding radio buttons is selected. (4) The user then selects whether the data type will be binary data or text. (5) When the user clicks on the OK button in the "Output ECG files in batch mode" window, the Select ECG Source window (previously described) appears. (6) The user selects where the data is to be retrieved from. Selecting "From whole directory" will extract the data from all folders in a selected directory. Selecting "From ECG database" will extract the data from a selected database class. The ECG parameters are saved when an OK button in the Select ECG Source is clicked on.

ECG files may be imported into the workstation by any conventional means, including but not limited to copying ECG files from a diskette, transferring ECG files from a PCMCIA card via local and wide area networks, wireless communication channels, and internet.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

What is claimed is:

1. A system comprising a computer, a display screen connected to said computer, and an operator interface connected to said computer, wherein said computer is programmed to perform the following steps:

retrieving raw ECG data from computer memory in response to a retrieve raw ECG data instruction input via said operator interface, said raw ECG data representing a plurality of ECG waveforms; and following said retrieving step, controlling said display screen to concurrently display first and second windows, said first window displaying said plurality of ECG waveforms, and said second window displaying an ECG waveform selected from said plurality of ECG waveforms.

wherein said second window comprises a plurality of virtual ECG analysis option buttons corresponding to a respective plurality of ECG analysis options and a virtual Run button, said computer being programmed to run at least a portion of a ECG analysis program on the waveform displayed in said second window in accordance with a ECG analysis option selected by clicking on one of said virtual ECG analysis buttons and in response to clicking on said virtual Run button, said clicking operations being performed via said operator interface, and wherein said computer is programmed to control said display screen to display a third window concurrently with said first and second windows, said third window displaying a set of parameter values in spreadsheet format if a parameter spreadsheet selection was previously inputted via said operator interface, said parameter values being derived by said ECG analysis program from said plurality of ECG waveforms in said first window in accordance with the ECG analysis option selected in said second window.

2. A system comprising a computer, a display screen connected to said computer, and an operator interface connected to said computer, wherein said computer is programmed to perform the following steps:

retrieving raw ECG data from computer memory in response to a retrieve raw ECG data instruction input via said operator interface, said raw ECG data representing a plurality of ECG waveforms; and following said retrieving step, controlling said display screen to concurrently display first and second windows, said first window displaying said plurality of ECG waveforms, and said second window displaying an ECG waveform selected from said plurality of ECG waveforms and a plurality of markers which intersect said ECG waveform in said second window, and said computer controls said display screen to displace a selected marker of said plurality of markers in response to a marker selection and in dependence on a move marker instruction input via said operator interface, wherein said second window comprises a plurality of virtual marker buttons corresponding to said plurality of markers, said marker selection comprising the step of clicking on one of said virtual marker buttons corresponding to said selected marker, and said move marker instruction comprises the steps of placing a cursor over said selected marker in said second window, activating said cursor and moving said cursor to a new position, said computer being further programmed to drag said selected marker to said new position when said moving cursor is active, and wherein said second window further comprises a plurality of virtual ECG analysis option buttons corresponding to a respective plurality of ECG analysis options and a virtual Run button, said plurality of ECG analysis options including an analysis with modified markers option, said computer being further programmed to run an ECG analysis program on the waveform displayed in said second window in accordance with said plurality of markers as modified in response to clicking on the virtual ECG analysis option button corresponding to said analysis with modified markers option followed by clicking on said virtual Run button, said clicking operations being performed via said operator interface, and wherein said computer is further programmed to control said display screen to display a third window concurrently with said first and second windows, said third window displaying an array of parameter values in spreadsheet format if a parameter spreadsheet selection was previously inputted via said operator interface, said parameter values being derived by said ECG analysis program from said plurality of ECG waveforms in said first window in accordance with the modified markers in said second window.

3. A system comprising a computer, a display screen connected to said computer, and an operator interface connected to said computer, wherein said computer is programmed to perform the following steps:

retrieving raw ECG data from computer memory in response to a retrieve raw ECG data instruction input via said operator interface, said raw ECG data representing a plurality of ECG waveforms; and following said retrieving step, controlling said display screen to concurrently display first and second windows, said first window displaying said plurality of ECG waveforms, and said second window displaying an ECG waveform selected from said plurality of ECG waveforms, wherein said computer is programmed to control said display screen to display a third window concurrently with said first and second windows, said third window displaying an array of parameter values in spreadsheet format if a parameter spreadsheet selection was previously inputted via said operator interface, said parameter values being derived by an ECG analysis program from data representing said plurality of ECG waveforms in said first window.

4. The system as recited in claim 3, wherein said third window displays an array of parameter identifiers in said spreadsheet format in response to input of a select parameter instruction via said operator interface, said parameter indentifiers corresponding to the parameter values displayed in said array of parameter values.

5. The system as recited in claim 4, wherein said computer is programmed to export selected parameter values from said array of parameter values in response to an export parameters instruction input and in dependence on a expert set of parameter identifiers selected via said operator interface.

6. The system as recited in claim 1, wherein said third window displays a chart overlying at least a portion of said spreadsheet in response to input of a display chart instruction via said operator interface, said chart comprising graphical data derived from at least some of said parameter values.

7. A system comprising a computer, a display screen connected to said computer, and an operator interface connected to said computer, said computer comprising memory for storing a mulitplicity of ray ECG files and a database comprising a respective record for each of said raw ECG files, each raw ECG file comprising data representing a plurality of waveforms, and each record comprising a respective patient identifier, a respective pathname to the corresponding raw ECG file, and respective parameter values characteristic of said waveforms of said corresponding raw ECG file, wherein said computer is programmed to perform the following steps:

loading a multiplicity of database records in working memory in response to activation of a load database records function via said operator interface; and controlling said display screen to concurrently display first and second windows, said first window displaying a field containing an identifier of a record in said database, and said second window displaying a plurality of ECG waveforms from a raw ECG file identified by a particular pathname in said record identified by said identifier displayed in said field.

8. The system as recited in claim 7, wherein said computer is programmed to control said display screen to change said second window to display a list of ECG analysis statements in response to input of an ECG analysis statement selection via said operator interface, said statement being derived by an ECG analysis program from said plurality of ECG waveforms in said first window.

9. A system comprising a computer, a display screen connected to said computer, and an operator interface connected to said computer, said computer comprising memory for storing a multiplicity of raw ECG files and a database comprising a respective record for each of said raw ECG files, each raw ECG file comprising data representing a plurality of ECG waveforms, and each record comprising a respective patient identifier, a respective pathname to the corresponding raw ECG file, and respective parameter values characteristic of said waveforms of said corresponding raw ECG file, wherein said computer is programmed to perform the following steps:

loading a multiplicity of database records in working memory in response to activation of a load database records function via said operator interface; and controlling said display screen to concurrently display first and second windows, said first window displaying a plurality of ECG waveforms from a raw ECG file identified by a pathname in one of said loaded database records, and said second window displaying an array of parameter values from said one database record in a spreadsheet format, wherein said computer is programmed to control said display screen to change said second window to display an array of parameter identifiers in said spreadsheet format in response to input of a select parameter instruction via said operator interface, said parameter identifiers corresponding to particular parameter values displayed in said array of parameter values.

10. The system as recited in claim 9, wherein said computer is programmed to export selected parameter values from said array of parameter values in response to an export parameters instruction input and in dependence on an export set of parameter identifiers selected via said operator interface.

11. The system as recited in claim 9, wherein said computer is programmed to control said display screen to change said second window to display a chart overlying at least a portion of said spreadsheet in response to input of a display chart instruction via said operator interface, said chart comprising graphical data derived from at least some of said parameter values.

12. A research workstation comprising:

a display screen;

an operator interface;

memory for storing raw ECG data representing a plurality of ECG waveforms;

means for retrieving said raw ECG data from said memory in response to a retrieve raw ECG data instruction input via said operator interface;

means for concurrently displaying said plurality of ECG waveforms in a first window and an ECG waveform selected from said plurality of ECG waveforms in second window on said display screen;

means for analyzing said ECG waveforms displayed in said first window, said analyzing means generating a multiplicity of parameter values; and means for displaying said parameter values in a spreadsheet format in a third window concurrently with said first and second windows.

13. A research workstation comprising:

a display screen;

an operator interface;

memory for storing records of raw ECG data representing a plurality of ECG waveforms;

means for retrieving raw ECG data in response to a retrieve raw ECG data instruction input via said operator interface;

means for analyzing said raw ECG data to generate a multiplicity of parameter values; and means for concurrently displaying said plurality of ECG waveforms in a first window and said mulitplicity of parameter values in spreadsheet format in a second window on said display screen.

14. The workstation as recited in claim 13, further comprising means for displaying an array of parameter identifiers in said spreadsheet format in said second window instead of said multiplicity of parameter values, said parameter identifiers corresponding to the parameter values.

15. The workstation as recited in claim 13, further comprising means for exporting selected parameter values from said multiplicity of parameter values in response to an export parameters instruction input and in dependence on an export set of parameter identifiers selected via said operator interface.

16. The workstation as recited in claim 13, further comprising means for displaying a chart overlying at least a portion of said spreadsheet in response to input of a display chart instruction via said operator interface, said chart comprising graphical data derived from at least some of said parameter values.

17. A research workstation comprising a built-in database and programming for presenting a graphical user interface for concurrent display of first, second and third windows, said first window having user-interactive areas that enable selection of a record in said database that corresponds to a file of physiological signal data, said second window displaying physiological signal waveforms corresponding to said physiological signal data of said file selected via said first window, and said third window presenting a spreadsheet of physiological signal parameters for said displayed physiological signal waveforms.

18. The workstation as recited in claim 17, further comprising programming for scrolling through records in said database in response to user interaction with one of said user-interface areas on said first window, and programming for changing data displayed in said second and third windows to correspond to each new record during scrolling.

19. The workstation as recited in claim 18, wherein said first window also displays information identifying the record and patient whose data is being displayed in said second and third windows, further comprising programming for changing the record and patient identifiers displayed in said first window to correspond to each new record during scrolling.

20. The workstation as recited in claim 17, further comprising programming for enabling adding, deleting and modifying of records in said database in response to user interaction with a database toolbar displayed as part of said graphical user interface.

21. The workstation as recited in claim 17, wherein said database comprises patient information, parameter data and path names for locating stored physiological signal waveform files.

22. The workstation as recited in claim 21, further comprising programming for automatically calculating QT dispersion based on physiological signal waveform data in selected files, and programming for automatically displaying the results of said QT dispersion calculation in a data field in said first window.

23. The workstation as recited in claim 17, further comprising programming for performing a search of said database in response to user interaction with a database toolbar displayed as part of said graphical user interface.

24. The workstation as recited in claim 17, further comprising programming for exporting selected data from said database to an external file in response to user interaction with a database toolbar displayed as part of said graphical user interface.

25. The workstation as recited in claim 17, further comprising:

programming for performing a search of said database in response to user interaction with a search popup window, said search popup window comprising fields for entering query parameters; and programming for displaying search results in said first window.

26. The workstation as recited in claim 25, further comprising programming for sorting said search results in accordance with a sorting methodology selected by user interaction with a sorting popup window linked to said search popup menu.

27. The workstation as recited in claim 17, wherein said database is an Open Database Connectivity (ODBC) database.

28. The workstation as recited in claim 17, wherein said physiological signals are ECGs.

29. A research workstation comprising a built-in database and programming for presenting a graphical user interface for concurrent display of first, second and third windows, said first window having user-interactive areas that enable selection of stored physiological signal data, said second window displaying physiological signal waveforms corresponding to physiological signal data selected via said first window, and said third window displaying a selected one of said displayed physiological signal waveforms with modifiable time markers and having user-interactive areas that enable a user to modify said modifiable time markers and then run a physiological signal re-analysis based on said user-modified time markers using physiological signal analysis.

30. The workstation as recited in claim 29, wherein said programming concurrently displays a fourth window as part of said graphical user interface, said fourth window presenting a spreadsheet of physiological signal parameters for said displayed physiological signal waveforms.

31. The workstation is recited in claim 29, further comprising programming for enabling said user to select one of a plurality of formats for display of said physiological signal waveforms in said second window in response to user interaction with a toolbar displayed as part of said graphical user interface.

32. The workstation as recited in claim 29, further comprising programming for a displaying in said third window, a selected one of said physiological signal waveforms displayed in said second window, said selected one of said physiological signal waveforms being selecting by a user input.

33. The workstation as recited in claim 32, wherein said user input is clicking on said selected physiological signal waveform in said second window.

34. The workstation as recited in claim 29, wherein said third window has user-interactive areas for enabling said user to select one of a plurality of physiological signal analysis options.

35. The workstation as recited in claim 30, further comprising programming for storing selected parameters in an external file in response to selection of parameters by user interaction with said fourth window.

36. The workstation as recited in claim 29, wherein said physiological signals are ECGs.

37. A research workstation comprising a built-in database and programming for presenting a graphical user interface for concurrent display of first, second and third windows, said first window having user-interactive areas that enable a search for records in said database that satisfy query parameters, each record corresponding to a respective file of physiological signal data, said second window dispalying physiological signal waveforms corresponding to physiological signal data of one of the files having a record satisfying said query parameters, and said third window presenting a spreadsheet of physiological signal parameters for physiological signal data of all of said files having records satisfying said query parameters.

38. The workstation as recited in claim 37, wherein said graphical user interface further comprises a user-interactive area for selecting one of a plurality of physiological signal analysis options, and said physiological signal parameters for physiological signal data presented in said third window were computed using said selected physiological signal analysis option.

39. The workstation as recited in claim 37, wherein said database is an Open Database Connectivity (ODBC) database.

40. The workstation as recited in claim 37, wherein said physiological signals are ECGs.

* * * * *